(12) United States Patent
Allen et al.

(10) Patent No.: US 7,115,256 B1
(45) Date of Patent: Oct. 3, 2006

(54) METHODS OF TREATING SCHIZOPHRENIA

(75) Inventors: Richard C. Allen, Flemington, NJ (US); Michael Cornfeldt, Morristown, NJ (US)

(73) Assignee: Titan Pharmaceuticals, Inc., Somerville, NJ (US)

( * ) Notice: Subject to any disclaimer, the term of this patent is extended or adjusted under 35 U.S.C. 154(b) by 0 days.

(21) Appl. No.: 09/289,576

(22) Filed: Apr. 9, 1999

(51) Int. Cl.
*A01N 66/00* (2006.01)
*A01N 65/00* (2006.01)

(52) U.S. Cl. .................................... 424/93.1
(58) Field of Classification Search ................ 435/325, 435/366; 424/93.1, 93.2, 93.21, 93.7
See application file for complete search history.

(56) References Cited

U.S. PATENT DOCUMENTS

| | | | |
|---|---|---|---|
| 4,935,365 A | 6/1990 | Nilsson et al. | |
| 5,447,948 A | 9/1995 | Seibyl et al. | |
| 5,618,531 A | 4/1997 | Cherksey | |
| 5,650,148 A | 7/1997 | Gage et al. | |
| 5,725,854 A | 3/1998 | Selawry | |
| 5,750,103 A | 5/1998 | Cherksey | |

FOREIGN PATENT DOCUMENTS

| WO | WO 98/56393 | 12/1998 |
|---|---|---|
| WO | WO-99/34834 A1 | 7/1999 |

OTHER PUBLICATIONS

National Institute of Mental Health, Schizophrenia, Jun. 1, 1999.*
Friedmann, T. Overcoming the obstacles to gene therapy. Sci. Am., Jun. 1997, pp. 96-101.*
Jackowski, A. Neural injury repair: hope for the future as barriers to effective CNS regeneration become clearer. Br. J. Neurosurgery 9: 303-317.*
Orkin and Motulsky. Report and recommendations of the panel to assess the NIH investment in research on gene therapy. Dec. 7, 1995.*
Verma et al. (1997) Gene therapy—promises, problems and prospects. Nature 389: 239-242.*
Bodkin, J.A. et al. (1996). "Treatment of Negative Symptoms in Schizophrenia and Schizoaffective Disorder by Selegiline Augmentation of Antipsychotic Medication: A Pilot Study Examining the Role of Dopamine," *Journal of Nervous and Mental Disease* 184(5): 295-301.
Andreasen, (1999). "Understanding the causes of schizophrenia," *New Eng. J. Med.* 340, No. 8, 645-647.
Angrist et al. (1992). "Central nervous system stimulants as symptomatic treatments for AIDS-related neuropsychiatric impairment," *J Clin. Psychopharm.* 12 No. 4, 268-272.
*Animal Cell Culture*. Edited by: Freshney, R. I., 1987 (Table of Contents).
*Antibodies: A Laboratory Manual* Edited by: Harlow et al., 1987. (Table of Contents).
Benoist et al. (1981). "In vivo sequence requirements of the SV40 early promoter region," *Nature* 290, 304-310.

Bohn et al. (1982). "Expression of phenylethanolamine N-methyltransferase in rat sympathetic ganglia and extra-adrenal chromaffin tissue," *Dev. Biol.* 89, 299-308.
*Current Protocols in Molecular Biology*. Edited by: Ausubel, F. M. et al., 1987 (Table of Contents).
Daniel et al. (1989). "The effect of apomorphine in regional cerebral blood flow in schizophrenia," *J. Neuropsych.* 1 No. 4, 377-384.
Daniel et al. (1991). "The effect of amphetamine on regional cerebral blood flow during cognitive activation in schizophrenia," *J. Neurosci.* 11 No. 7, 1907-1917.
Doering et al. (1984). "Isolation and transplantation of oligodendrocyte precursor cells," *J. Neurol. Sci.* 63 No. 2, 183-196.
Eyre. (1980). "Collagen: molecular diversity in the body's protein scaffold," *Science* 207, 1315-1322.
Freed et al. (1981). "Transplanted adrenal chromaffin cells in rat brain reduce lesion-induced rotational behavior," *Nature* 292 No. 5281, 351-352.
Gage et al. (1987). "Grafting genetically modified cells to the brain: possibilities for the future," *Neurosci.* 23 No. 3, 795-807.
Gash et al. (1986). "Amitotic neuroblastoma cells used for neural implants in monkeys," *Science* 233, 1420-1422.
Goldberg et al. (1994). "The effects of clozapine on neurocognition: an overview," *J. Clin. Psychiatry* 55:9 (suppl. B 88-90).
Greene e al. (1975). "Neuronal properties of hybrid neuroblasoma X sympathetic ganglion cells," *Proc. Natl. Acad. Sci. U.S.A.* 72 No. 12, 4923-4927.
Gross-Jendroska et al. (1990). "RPE-Stromal interactions modulate hyaluronic acid deposition: Role of HA-stimulating activity," *Investigative Opthamol.* ARVO Suppl. 31, No. 4, 102.
Gumpel et al: (1984). "Survival and differentiation of oligodendrocytes from neural tissue transplanted into new-born mouse brain," *Neurosci. Lett.* 37 No. 3, 307-311.
Gupta et al. (1985) "Differentiation characteristics of human neuroblastoma cells in the presence of growth modulators and antimitotic drugs," *Dev. Brain Res.* 19, 21-29.
Hamer et al. (1982). "Regulation in vivo of a cloned mammalian gene: cadmium induces the transcription of a mouse metallothionein gene in SV40 vectors," *J. Mol. Appl. Genet.* 1 No. 4, 273-288.
Jaffe et al. (1990). "Anti-transferrin receptor immunotoxin inhibits human RPE cell proliferation," *Investigative Opthamol.* ARVO Suppl. 31, No. 4, 69.
Jentsch et al. (1997). "Enduring cognitive deficits and cortical dopamine dysfunction in monkeys after long-term administration of phencyclidine," *Science* 277, 953-955.
Karlsson. et al. (1995), "Lack of apparent antipsychotic effect of the D1-dopamine receptor antagonist SCH39166 in acutely ill schizophrenic patients," *Psychopharmacology* 121, 309-316.

(Continued)

*Primary Examiner*—Anne-Marie Falk
(74) *Attorney, Agent, or Firm*—Morrison & Foerster LLP

(57) ABSTRACT

The invention provides methods for the treatment of abnormal psychiatric states, particularly the negative symptoms of schizophrenia and extrapyramidal side effects (EPS) of antipsychotic drugs. The inventive methods relate to the administration of therapeutic cells (which produce dopamine or dopamine precursors) adhered to support matrices to subjects suffering from the negative symptoms of schizophrenia and/or EPS. The therapeutic cells may be coadministered with cells which protect the therapeutic cells from immune rejection and/or cells which produce neurotrophic factors which improve the viability of the therapeutic cells.

9 Claims, No Drawings

OTHER PUBLICATIONS

Keefe et al. (Sep. 1995). "A pen-and-paper human analogue of a monkey prefrontal cortex activation task: spaial working memory in patients with schizophrenia," *Schizophr. Res.* 17 No. 1, 25-33.

Kimhi et al. (1976). "Maturation of neuroblastome cells in the presence of dimethysulfoxide," *Proc. Natl. Acad. Sci. U. S. A.* 73 No. 2, 462-466.

Kimhi. *Excitable Cells in Tissue Culture.* Edited by: Nelson, P. G. et al., New York: Plenum. 1977. 173-245.

Kovacic et al. (1982). "A monkey model of tardive dyskinesia (TD): evidence that reversible TD may turn into irreversible TD," *J. Clin. Psychopharmacol.* 2 No. 5, 305-307.

Li et al. (1988). "Inherited retinal dystrophy in the RCS rat: prevention of photoreceptor degeneration by pigment epithelial transplantation," *Exp. Eye Res.* 47 No. 6, 911-917.

Lopez et al. (1989). "Transplanted retinal pigment epithelium modifies the retinal degeneration in the RCS rat," *Invest. Ophthamol. Vis. Sci.* 30 No. 3, 586-588.

Lui et al. (1990). "Stimulation of inositol phosphate formation in cultured human retinal pigment epithelial cells," *Investigative Opthamol.* ARVO Suppl. 31, No. 4, 371.

Martin et al. (1985). "The genetically distinct collagens," *TIBS* 10, 285-287.

McKnight. (1982). "Fucntional relationships between transcriptional control signals of the thymidine kinase gene of herpes simplex virus," *Cell* 31(2 pt. 1), 355-365.

*Methods in Enzymology.* Edited by: Jakoby et al., 1979. (Table of Contents).

Moghaddam et al. (1997). "Activation of glutamatergic neurotransmission by ketamine: A novel step in the pathway from NMDA receptor blcokade to dopaminergic and cognitive disruptions associated with the prefrontal cortex," *J. Neurosci.* 17 No. 8, 2921-2927.

Moghaddam et al. (1998). "Reversal of phencyclidine effects by a group II metabotropic glutamate receptor agonist in rats," *Science* 281, 1349-1352.

Notter et al. (1986). "Neuronal properties of monkey adrenal medulla in vitro," *Cell Tiss. Res.* 244 No. 1, 69-76.

Olson et al. (1980). "Chromaffine cells can innervate brain tissue: evidence from intraocular double grafts," *Exp. Neurol.* 70 No. 2, 414-426.

Padgett et al. (1990). "Metalloproteinase and metallproteinase inhibitor secretion by human and RCS rat retinal pigment epithelium in culture," *Investigative Opthamol.* ARVO Suppl. 31, No. 4, 72.

*PCR 2: A Pratical Approach.* Edited by: McPherson, M. J. et al., 1995. (Table of Contents).

Piercey et al. (1988). "Dramatic limbic and cortical effects mediated by high affinity PCP receptors," *Life Sci.* 43 No. 4, 379-385.

Prasad et al. (1974) "Cyclic AMP and the differentiation of Neuroblastoma cells in culture," *Control of Proliferation in Animal Cells.* Edited by: Clarkson, B. et al., Cold Spring Harbor Laboratory Press. 581-594.

Prockop et al. (1979). "The biosynthesis of collagen and its disorders (first of two parts)," *New Engl. J. Med.* 301 No. 1, 13-23.

Prockop et al. (1979). "The biosynthesis of collagen and its disorders (second of two parts)," *New Engl. J. Med.* 301 No. 2, 77-85.

Puro et al. (1976). "On the specificity of synapse formation," *Proc. Natl. Acad. Sci. U. S. A.* 73 No. 10, 3544-3548.

Purohit et al. (1993). "Severe cognitive impairment in elderly schizophrenic patients: a clinicopathological study," *Biol. Psych.* 33 No. 4, :255-260.

Rosenberg et al. (1988). "Grafting genetically modifies cells to the damaged brain: restorative effects og NGF expression," *Science* 242, 1575-1578.

Sambrook et al. *Molecular Cloning: A Laboratory Manual.* 2nd ed. 1989. (Table of Contents).

Scherer et al. (1992). "Human dopa decarboxylase: localization to human chromosome 7p11 and characterization of hepatic cDNAs," *Genomics* 13 No. 2, 469-471.

Shimohama et al. (1989). "Grafting genetically modified cells into the rat brain: characteristics of *E. coli* β-galactosidase as a reporter gene," *Mol. Brain Res.* 5 No. 4, 271-278.

*Sigma Cell Culture.* Sigma Chemical Co. St. Louis. 1991. 162-163.

Song et al. (1990). "Propagation of fetal human RPE cells: Preservation of original culture morhphology after serial passage," *J. Cell. Physiol.* 148, 196-203.

Stromberg et al. (1985). "Chronic implants of chromaffin tissue into the dopamine-denervated striatum. Effects of NGF on graft survival, fiber growth and rotational behavior," *Exp. Brain Res.* 60 No. 2, 335-349.

Unsicker. (1985). "Embryologic development of rat adrenal medulla in transplant to the anterior chamber of the eye," *Dev. Biol.* 108 No. 2, 259-268.

Wickelgren (1998). "A new route to treating schizophrenia?" *Science* 281, 1264-1265.

Wolff et al. (1989). "Grafting fibroblasts genetically modified to produce L-dopa in a rat model of Parkinson disease," *Proc. Natl. Acad. Sci. U. S. A.* 86 No. 22, 9011-9014.

Wu et al. (1978). "Synthetic oligodeoxynucleotides for analyses of DNA structure and function," *Prog. Nucl. Acid. Res. Molec. Biol.* 21, 101-141.

Watts, R.L. et al. (2001)."Stereotaxic Intrastriatal Implantation of Retinal Pigment Epithelial Cells Attached to Microcarriers in Advanced Parkinson Disease (PD) Patients: A Pilot Study," *Presented at the XIV International Congress on Parkinson's Disease, Helsinki* Abstract P-305:2 pages total.

Subramanian, T. et al. (Apr. 23-26, 1998). "Effects of Stereoetactic Intrastriatal Transplantation of Human Retinal Pigmentd Epithelial (hRPE) Cells Attached to Gelatin Microcarriers on Parkinsonian Motor Symptoms in Hemipakinsonian (HP) Monkeys," *Presented at the Fifth Annual Conference of the American Society for Neural Transplantation, Clearwater*, Florida Abstracts 2-5:1 page total.

Subramanian, T. et al. (Oct. 10-14, 1998). "Intrastriatal Transplantation of Human retinal Pigmented Epithelial Cells Attached to Gelatin Microcarriers (hRPE-GM) Improves Parkinsonian Motor Signs in Hemiparkinsonian (HP) Monkeys," *Submitted for the 5th International Congress of Parkinson's Disease and Movement Disorders, New York City, New York*:1 page total.

Potter, B.M. (Oct. 1997). "Functional Effects of Intrastriatal HRPE Grafts in Hemiparkinsinian Rats is Enhanced by Adhering to Microcarrier Beads," *Abs. Soc. Neurosci., 27th Annual Meeting, New Orleans* Abstract 778.10:1 page total.

Subramanian, T. et al. (1999). "Blinded Placebo-Controlled Trial to Assess the Effects of Striatal Transplantation of Human Retinal Pigmented Epithelial Cells Attached to Microcarriers (hRPE-M) in Pakinsonian Monkeys," *Abstract/Parkinsonism and Related Disorders* 5(Abstract P-WE-050):S111.

Davis, K.L. et al. (Nov. 1991). "Dopamine in Schizophrenia: A Review and Reconceptualization," *Am. J. Psychiatry* 148(11):1474-1486.

Domino, E.F. (1985). "Induction of Tardive Dyskinesia in *Cebus appella* and *Macaca speciosa* Monkeys: A Review," *Psychopharmacology Suppl.* 2:217-223.

Gunne, L.M. and Bárány, S. (1976). "Haloperido1-Induced Tardive Dyskinesia in Monkeys," *Psychopharmacology* 50:237-240.

Sawaguchi, T. and Goldman-Rakic, P.S. (Feb. 22, 1991). "D1 Dopamine Receptors in Prefrontal Cortex: Involvement in Working Memory," *Science* 251:947-950.

Wilson, F.A.W. et al. (Jun. 25, 1993). "Dissociation of Object and Spatial Processing Domains in Primate Prefrontal Cortex," *Science* 260:1955-1958.

Abi-Dargham, A. et al. (2003). "Prefrontal DA Transmission at $D_1$Receptors and the Pathology of Schizophrenia", *The Neuroscientist*, vol. 9, No. 5, pp. 404-416.

Fernández-Ruiz et al., Psychopharmacology (1999) 147:104-107.

Watts et al., J. Neural Transm. Suppl. (2003) 65:215-227.

Inanaga, K. et al. (1975). "Double-Blind Controlled Study of L-Dopa Therapy in Schizophrenia," *Folia Psychiatrica et Neurologica Japonica* 29(2):123-143, specifically p. 123, second column, first paragraph and p. 140, second column, first paragraph.

International Search Report mailed Nov. 7, 2000 for PCT Application No. PCT/US0/07514, 3 pages.

\* cited by examiner

METHODS OF TREATING SCHIZOPHRENIA

TECHNICAL FIELD

The invention relates generally to the treatment of psychiatric disorders, and particularly to methods of treating negative symptoms of schizophrenia and/or certain extrapyramidal side effects (EPS) of antipsychotics by administering an effective number of cells, adhered to a support matrix, which are capable of producing dopamine or a dopamine precursor to a subject suffering from schizophrenia.

BACKGROUND

Disorders of the nervous system comprise a wide variety of conditions, and can generally be separated into "neurological disorders" and "psychiatric disorders". Neurological disorders can be characterized as the product of the death of nervous system cells. Examples of neurological disorders include Parkinson's Disease, which involves the death of dopaminergic neurons, Alzheimer's disease, in which cholinergic neurons are lost, and multiple sclerosis, in which neurons and glia are killed in an autoimmune process. Psychiatric disorders, on the other hand, are the result of dysregulation of neurons, which can result in abnormal levels of various neurochemicals and/or abnormal responsiveness to neurochemicals.

Psychiatric disorders, such as schizophrenia, are major public health concerns. Schizophrenia, for example, affects approximately 2 million Americans. At any particular time, about 20% of the hospital beds in the U.S. are occupied by schizophrenic patients. The illness usually develops between adolescence and age 30 and is characterized by positive symptoms (delusions or hallucinations), negative symptoms (blunted emotions and lack of interest) and disorganized symptoms (confused thinking and speech or disorganized behavior and perception). Additionally, cognitive deficits are also frequently observed, particularly in elderly schizophrenia patients (Purohit et al., 1993, *Biol. Psychiatry* 33(4): 255–260). For some patients, the disorder is lifelong, while others may have periodic episodes of psychosis.

The causes of schizophrenia are essentially unknown. Although it is believed to have a genetic component, environmental factors appear to influence the onset and severity of the disease. Neuropathological changes in schizophrenics may include enlargement of the lateral ventricles, cavities in the brain which are part of the cerebrospinal fluid system. Sometimes, there is a decrease in overall brain mass.

A number of animal models have been developed for schizophrenia, utilizing both non-primate (rat) and primate (monkey) animals. In one commonly used animal model of schizophrenia, phencyclidene (PCP) is chronically administered to the animal subjects, resulting in dysfunctions similar to those seen in schizophrenic humans (Jentsch et al., 1997, *Science* 277:953–955; Piercey et al., 1988, *Life Sci.* 43(4):375–385).

Several different theories have been developed regarding the etiology of schizophrenia, including the dopaminergic, glutamatergic, and cholinergic theories of schizophrenia. The dopamine hypothesis posits that positive symptoms result from excess function of the neurotransmitter dopamine in the mesolimbic area of the brain. This hypothesis is based largely on indirect, pharmacological evidence that (1) dopamine-antagonizing drugs are effective antipsychotic agents; (2) dopamine-mimicking drug exacerbate schizophrenic symptoms and (3) certain symptoms of acute paranoid schizophrenia can be elicited in non-schizophrenics by amphetamine, a drug that activates dopamine systems. Conversely, negative symptoms have been associated with regionally localized dopamine deficits in the prefrontal cortex.

The glutamate hypothesis is based, among other things, the actions of phencyclidine (PCP) in the brains of abusers. PCP, which induces a number of symptoms also found in schizophrenia, blocks the N-methyl-D-aspartate (NMDA) receptor, through which glutamate exerts some of its effects. Additionally, observations from the phencyclidine (PCP) animal model of schizophrenia, indicate that glutamate is dramatically increased in the brains of rats chronically dosed with PCP (Moghaddam et al., 1997, *J. Neurosci.* 17:2921). Inhibition of the rise in glutamate levels with a metabotropic glutamate receptor agonist blocked a variety of schizophrenia symptoms in PCP-dosed rats, including hyperactive behavior, head turning, and memory deficits (Moghaddan et al., 1998, *Science* 281:1349–1352).

Current treatments for schizophrenia include antipsychotic drugs; electric shock treatment for severe catatonia, depression, or elation; and psychotherapy. Antipsychotic drug treatments generally include both dopamine and acetylcholine antagonists (anticholinergics), although anticholinergics are generally used to treat extrapyramidal side effects (EPS) of commonly used dopamine antagonists, rather than the disorder itself. EPS induced by dopamine antagonists result from dopamine blockade in the striatum and include dyskinesias, especially tardive dyskinesia, which are characterized by uncontrolled movements. In most cases, tardive dyskinesia resolves following discontinuation of dopamine agonist drug therapy, but some patients continue to experience dyskinesia long after termination of dopamine antagonist therapy.

Clopazine, an antipsychotic that affects several receptor systems, is currently viewed as the "gold standard" of drug treatment for schizophrenia. However, although clopazine seems to ameliorate certain symptoms (e.g.; verbal fluency, reaction time and attention), it appears to have an adverse effect on higher level executive functions, such as working memory ability and visual memory. Goldberg et al. (1994) *J. Clin. Psychiatry* 55:9 (suppl. B). Moreover, many dopamine antagonist antipsychotic drugs are not as effective at controlling the "negative" symptoms, as compared to the "positive" symptoms of schizophrenia (Angrist et al., 1982, *Psychopharm.* 78:128–130).

U.S. Pat. No. 5,447,948 asserts that dopamine reuptake inhibitors are useful in treating schizophrenic patients suffering from negative symptoms. However, dopamine reuptake inhibitors oppose the effects of clopazine and other dopamine antagonists, potentially nullifying the activity of this group of drugs in the treatment of the positive symptoms of schizophrenia.

U.S. Pat. No. 5,618,531 describes methods of increasing the viability of cells which are administered to the brain or spinal cord of a mammalian subject by attaching the cells to a support matrix. It is indicated that the cells may be used to "neurological disorders," but not psychiatric disorders. As commonly understood in the art, "neurological disorders" are disorders of the nervous system which involve death or major dysfunction of cells of the nervous system, while "psychiatric disorders" involve the misregulation of cells of the nervous system. For example, Parkinson's disease, which involves the death and dysfunction of dopaminergic neurons, is a neurological disorder, while schizophrenia, which involves the misregulation of neurotransmitter levels, is a psychiatric disorder.

In sum, there remains a need in the art for an effective treatment of the symptoms of schizophrenia, particularly the negative symptoms of schizophrenia and cognitive defects associated with schizophrenia, which will not interfere with treatments for the positive symptoms of the disorder. Additionally, there exists a need in the art for an effective treatment for tardive dyskinesia and other EPS.

SUMMARY OF THE INVENTION

The invention relates to methods of treating schizophrenia, particularly the negative symptoms of schizophrenia, by administering therapeutic cells which produce dopamine to a subject having schizophrenia. The therapeutic methods of the invention provide treatments for the negative symptoms of schizophrenia which do not interfere with contemporaneous, pharmacological treatments for the positive symptoms of schizophrenia. The invention also provides methods for the treatment of EPS, particularly tardive dyskinesia (TD), also by the administration of therapeutic cells.

In one aspect, the invention provides methods for treating symptoms of schizophrenia, particularly the negative symptoms of schizophrenia and cognitive deficits associated with schizophrenia, by administering therapeutic cells adhered to a support matrix (cell/support complex) to the subject. The therapeutic cells may be paraneural cells, neural cells, cells engineered by somatic cell hybridization, cells derived from the adrenal medulla, cells that have been genetically engineered to produce dopamine, or any other cells which produce dopamine. The support matrix is a non-encapsulating particulate support.

In another aspect, the invention provides methods in which protective cells (cells which produce an immunologically privileged site) are administered with the therapeutic cells. Alternately, the therapeutic cells may have the properties of protective cells.

In a further aspect, the invention provides methods in which support cells, which provide factors which improve the viability or function of the therapeutic cells, are administered with the therapeutic cells. A combination of therapeutic cells, protective cells, and support cells for administration to the patient is also contemplated.

In another embodiment, the invention provides methods for improving cognitive deficits associated with schizophrenia, particularly elderly schizophrenia patients. Cognitive deficits are treated by the administration of therapeutic cells, or a combination of therapeutic cells with protective cells and/or support cells, adhered to a support matrix, to the brain of a subject suffering from schizophrenia-associated cognitive deficits. Administration of the therapeutic cells results in an improvement in cognitive function in the subject.

In further embodiments, the invention provides methods for the treatment of EPS such as tardive dyskinesia, tardive dystonia and tardive akathisia, particularly tardive dyskinesia. In accordance with the invention, EPS are treated by administration of therapeutic cells which produce dopamine, adhered to a substrate, to a subject. The therapeutic cells may be administered with protective cells, or have the properties of protective cells. Additionally, support cells may be administered with the therapeutic cells.

Also provided are pharmaceutical compositions comprising the therapeutic cells adhered to a support matrix. The pharmaceutical compositions may optionally comprise protective cells, support cells, or both.

In a further embodiment, the invention provides kits which may be utilized for practicing the instant inventive methods. The kits comprise therapeutic cells and a support matrix, and may additionally include protective cells, support cells, or both protective cells and support cells.

As will become apparent, preferred features and characteristics of one aspect of the invention are applicable to any other aspect of the invention.

DETAILED DESCRIPTION OF THE INVENTION

The present invention provides methods for treating the negative symptoms of schizophrenia by administration of cells into one or more sites in the central nervous system (CNS) of a subject suffering from the symptoms of schizophrenia, particularly negative symptoms of schizophrenia or cognitive deficits associated with schizophrenia. Cognitive deficits associated with schizophrenia may also be treated in accordance with the invention by the administration of therapeutic cells. The invention also provides methods for the treatment of EPS, particularly tardive dyskinesia, by administration of cells into one or more sites in the CNS of subject suffering from the symptoms of EPS such as tardive dyskinesia (TD). In accordance with the methods of the invention, cells which produce dopamine ("therapeutic cells") are introduced into the brain of a subject suffering from the negative symptoms of schizophrenia, cognitive deficits associated with schizophrenia, and/or EPS. The therapeutic cells are normally administered adherent to a microcarrier (cell/support complex) when administered to the subject, and can be administered with other cells. The instant invention is advantageous for the treatment of schizophrenia, particularly for the treatment of the negative symptoms of schizophrenia, cognitive deficits associated with schizophrenia, particularly in elderly schizophrenics, and EPS (e.g., TD) associated with the administration of antipsychotic drugs.

The instant methods may be used as a "stand alone" therapy, but are also contemplated for use in combination with other therapies. In particular, it is contemplated that the instant methods may be utilized in combination with standard schizophrenia therapies, such as clozapine. It is further contemplated that treatment of a subject in accordance with the invention will result in "cross-talk" within the brain of the subject, resulting in an improvement in positive symptoms suffered by the subject, independent of any improvement in positive symptoms due to treatment with antipsychotic drugs. Accordingly, the invention also provides methods for alleviating negative and positive symptoms of schizophrenia.

The practice of the present invention will employ, unless otherwise indicated, conventional techniques of molecular biology, microbiology, cell biology and recombinant DNA, which are within the skill of the art. See, e.g., Sambrook et al., MOLECULAR CLONING: A LABORATORY MANUAL, 2nd edition (1989); CURRENT PROTOCOLS IN MOLECULAR BIOLOGY, (F. M. Ausubel et al. eds., 1987); the series METHODS IN ENZYMOLOGY (Academic Press, Inc.); PCR 2: A PRACTICAL APPROACH (M. J. McPherson, B. D. Hames and G. R. Taylor eds., 1995); ANIMAL CELL CULTURE (R. I. Freshney. Ed., 1987); and ANTIBODIES: A LABORATORY MANUAL (Harlow et al. eds., 1987).

Definitions

As used herein, the term "schizophrenia" is intended to include the group of mental disorders characterized by disruptions in thinking and perception. In a clinical evaluation, schizophrenia is commonly marked by "positive symptoms" such as auditory hallucinations (especially hearing voices), disorganized thought processes and delusions as well as "negative symptoms" which include affective flattening, alogia, avolition, and anhedonia.

As used herein, "the negative symptoms of schizophrenia" refer to a class of symptoms of schizophrenia which can be considered to reflect a 'loss' in functional, directed thought or activity. Negative symptoms of schizophrenia are well known in the art, and include affective flattening (characterized by, for example, an immobile and/or unresponsive facial expression, poor eye contact and reduced body language), alogia ('poverty of speech' or brief, laconic and/or empty replies), avolition (characterized by a reduced or absent ability to initiate and carry out goal-directed activities), anhedonia (loss of interest or pleasure), social withdrawal, apathy and other negative symptoms known to those of skill in the art. The negative symptoms of schizophrenia may be assessed using any methodology known in the art including, but not limited to, the Brief Psychiatric Rating Scale (BPRS), the Positive and Negative Symptom Scale (PANSS), the Rorschach Schizophrenia Index (SCZI), and the Scale for the Assessment of Negative Symptoms (SANS). Some of these methods may also be used to assess positive symptoms (e.g., BPRS, PANSS and SCZI), although methods for specifically assessing positive symptoms are also available (e.g., the Scale for the Assessment of Positive Symptoms, or PANS).

As used herein "cognitive deficits associated with schizophrenia" refers to cognitive deficits in schizophrenia patients. Cognitive deficits include, but are not limited to deficits of working memory, visuospatial memory, and low performance on 'frontal' neuropsychological tests such as the Wisconsin Card Sorting Test (WCST).

The term "support matrix" includes any material to which cells adhere following in vitro incubation, and on which cells can grow, and which can be implanted into a mammalian brain without producing a toxic reaction, or an inflammatory or gliosis reaction which would destroy the implanted cells or otherwise interfere with their biological or therapeutic activity. Such materials may be synthetic or natural chemical substances or substances having a biological origin. The matrix materials include, but are not limited to, glass and other silicon oxides, polystyrene, polypropylene, polyethylene, polyvinylidene fluoride, polyurethane, polyalginate, polysulphone, polyvinyl alcohol, acrylonitrile polymers, polyacrylamide, polycarbonate, polypentene, polypentane, nylon, amylases, gelatin, modified (e.g., crosslinked) gelatin, collagen, natural and modified polysaccharides, including dextrans and celluloses (e.g. nitrocellulose), agar, and magnetite.

Either resorbable or non-resorbable materials may be used. Also intended are extracellular matrix materials, which are well-known in the art (see below). Extracellular matrix materials may be obtained commercially or prepared by growing cells which secrete such a matrix, removing the secreting cells, and allowing the cells which are to be transplanted to interact with and adhere to the matrix.

As used herein, the term "therapeutic cell" refers to a cell which produces dopamine or a precursor of dopamine (e.g., L-DOPA). Therapeutic cells may be of neural origin, paraneural cells such as retinal pigmented epithelium (RPE) cells and chromaffin cells, cells engineered by somatic cell hybridization, cells derived from the adrenal medulla, cells that have been genetically engineered to produce biologically active factors, and any other cells which produce dopamine or a dopamine precursor. In some cases, therapeutic cells will also have the attributes of protective cells (e.g., RPE cells). Therapeutic cells are preferably "species matched" (derived from the same species as the subject), but may be derived from any species, preferably a mammalian species.

A "paraneural cell" is a cell which is derived from the embryonic neural crest. Examples of paraneural cells include retinal pigmented epithelium (RPE) cells and cells derived from the adrenal medulla, such as adrenal chromaffin cells.

A "cell which produces an immunologically privileged site" is a cell which produces a locally immunosuppressive environment. A cell which produces an immunologically privileged site may also be known as a "protective cell". A locally immunosuppressive environment may be produced by the expression of anti-inflammatory or immunosuppressive molecules such as Fas ligand (Fas L), transforming growth factor beta (TGF-$\beta$) and/or other molecules known in the art. Cells which produce an immunologically privileged site include cells which naturally produce an immunologically privileged site, such as RPE cells and Sertoli cells, and cells which have been genetically modified to produce an immunologically privileged site by, for example, expressing Fas L or TGF-$\beta$. Protective cells are preferably species matched, but may be derived from any species, although preferably a mammalian species.

The term "support cell", as used herein, refers to a cell which produces factors that improve the viability of the therapeutic cells. Support cells may produce soluble factors, such as neurotrophic factors or other factors (e.g., growth factors), or they may produce extracellular matrix or other insoluble factors which improve the viability of the therapeutic cells. Suitable support cells for use in the instant invention include glial cells, which naturally 'support' neurons, and cells genetically engineered to act as support cells by, for example, producing a beneficial neurotrophic factor, such as NGF.

As used herein, "treatment" is an approach for obtaining beneficial or desired clinical results. For purposes of this invention, beneficial or desired clinical results include, but are not limited to, alleviation of symptoms associated with the psychiatric disorder, diminishment of the extent of the disorder, stabilized (i.e. not worsening) state of disorder, delay or slowing of disorder progression.

An "effective amount" or "effective number" is an amount or number sufficient to effect beneficial or desired therapeutic results. An effective amount can be administered in one or more administrations. For purposes of this invention, an effective amount is that amount which achieves the desired result, namely amelioration, stabilization, palliation or slowing of the mental disorder.

As used herein, the term "comprising" and its cognates are used in their inclusive sense; that is, equivalent to the term "including" and its corresponding cognates.

The term "subject" refers to a mammal, preferably a human.

An "expression vector" is a DNA construct which (due to the presence of appropriate transcriptional and/or translational control sequences) is capable of expressing a DNA (or cDNA) molecule which has been cloned into the vector and of thereby producing a polypeptide or protein in the therapeutic cell. Expression of the cloned sequences occurs when the expression vector is introduced into an appropriate host cell. An appropriate mammalian host cell would be any an cell capable of expressing the cloned sequences. Procedures for preparing cDNA and for producing a genomic library are disclosed by Sambrook et al. (supra).

Two DNA sequences (such as a promoter region sequence and a coding sequence) are said to be operably linked if the nature of the linkage between the two DNA sequences does not (1) result in the introduction of a frame-shift mutation, (2) interfere with the ability of the promoter region sequence to direct the transcription of the coding sequence, or (3) interfere with the ability of the coding sequence to be transcribed by the promoter region sequence. A promoter region would be operably linked to a DNA sequence if the promoter were capable of effecting transcription of that DNA sequence.

It should be noted that, as used herein, the singular form "a", "an" and "the" include plural references unless the context clearly dictates otherwise.

The present invention provides, in one aspect, methods for treating the negative symptoms of schizophrenia. In accordance with the instant invention, the negative symptoms of schizophrenia are treated by administering a cell/support complex comprising therapeutic cells that supply dopamine or a dopamine precursor adhered to a support matrix (cell/support complex) to the subject. The cell/support complex is generally administered directly into the brain by injection or implantation. The cell/support complex may be administered at one or more sites in the subject, and may be administered on a single administration or in multiple administrations. After completion of administration, the negative symptoms of schizophrenia are alleviated, ameliorated or eliminated. Alleviation, amelioration, or elimination of the negative symptoms of schizophrenia can be measured using any of the tests, scales, or indexes known in the art, such as the BPRS, SANS or PANSS.

In another aspect, the instant invention provides methods for treating the negative symptoms of schizophrenia by administering a cell/support complex comprising therapeutic cells in combination with cells which produce an immunologically privileged site ("protective cells"), although in certain other embodiments the therapeutic cells have the properties of protective cells. If the therapeutic cells are combined with separate protective cells, both types of cells are normally administered as a cell/support complex and are generally administered directly into the subject brain by injection or implantation.

The therapeutic cells, optionally with accompanying protective cells, are administered to subjects suffering from the negative symptoms of schizophrenia. Administration of the therapeutic cells (with or without protective cells) results in alleviation of the symptoms of the negative symptoms of schizophrenia.

Preferably, the cells are administered directly to the brain by injection or implantation. The cells are preferably administered to one or more sites in the prefrontal cortex. Preferably, the cells are administered to the prefrontal cortex in a bilaterally-symmetrical pattern (i.e., at matching sites in the left and right prefrontal cortex). The administration of the therapeutic cells results in alleviation of the symptoms of schizophrenia, particularly negative symptoms.

In another aspect, the invention provides methods of alleviating cognitive deficits associated with schizophrenia, particularly in elderly schizophrenia patients. Therapeutic cells are administered in a cell/support complex by injection or implantation into the prefrontal cortex of the subject's brain, particularly the dorsolateral prefrontal cortex. As with the instant methods for the treatment of the negative symptoms of schizophrenia, cognitive deficits may be treated by the administration of therapeutic cells in a cell/support complex with protective cells and/or support cells. Administration of therapeutic cells in a cell/support complex results in improvements in cognitive function.

The invention also provides methods for the treatment of extrapyramidal side effects (EPS). In accordance with the invention, a cell/support complex comprising therapeutic cells which produce dopamine or a dopamine precursor adhered to a support matrix are administered to a subject suffering from EPS (such as tardive dyskinesia, tardive dystonia and/or tardive akathisia). The therapeutic cells may optionally be administered in combination with protective cells. Preferably, the cells are administered by implantation or injection into one or more sites in the striatal area of the subject's brain. Preferably, the cells are administered in a bilaterally-symmetrically pattern.

Cells

Therapeutic cells, in accordance with the instant invention, produce dopamine or a dopamine precursor (e.g., L-DOPA). Cells useful in the practice of various aspects of this invention include cells of neural origin, paraneural cells such as RPE cells and chromaffin cells, cells engineered by somatic cell hybridization, cells derived from the adrenal medulla and cells that have been genetically engineered to produce biologically active factors. Neural and paraneural cells are preferred cells for use in the instant invention.

Typically, a cell used in the instant invention will be selected for its ability to produce dopamine or a dopamine precursor. Alternately, a cell may be selected for other properties (such as ease of propagation in vitro) and genetically engineered to produce the desired biologically active compound.

Generally, cells for use in accordance with the invention are post-mitotic or of very low or controlled mitotic potential when administered to the subject. As will be understood by one of skill in the art, the introduction of actively dividing cells into the cranium should be avoided. Introduction of actively dividing cells into the cranium of a subject can lead to the formation of a tumor, which can damage or destroy structures in the subject's brain due to compressive damage.

A preferred cell for use in the instant invention is a paraneural cell. Retinal pigmented epithelial (RPE) cells, which are found as a monolayer between the retina and uvea and which produce dopamine and other factors, are a preferred paraneural cell (Song et al., 1990, *J. Cell. Physiol.* 148:196–203). Methods of isolating and culturing human RPE cells are known in the art (for example, as described in Liu et al., 1988, *Exp. Eye Res.* 47:911–917; Lopez et al., 1989, *Invest. Ophthamol. Vis. Sci.* 30:586–588; and Lui et al., 1990, *Investigative Ophthamol.*, ARVO Supplement). RPE cells can be isolated for any source known in the art, and are preferably human.

Another example of a cell of paraneural origin is an adrenal medullary chromaffin cell. The cells which form the mammalian adrenal medulla are derived from the neural crest and possess the potential to develop along either neuronal or endocrine lines of differentiation (Bohn et al., 1981, supra, and 1982, *Devel. Biol.* 89:299–308; Unsicker, 1985, *Develop. Biol.* 108:259–268). Mammalian chromaffin cells from the adrenal medulla, when removed from adrenal cortical influences and exposed to nerve growth factor (NGF), change from an endocrine to a neuronal phenotype (Notter et al., 1986, *Cell Tiss. Res.* 244:69–70; Stromberg et al., 1985, *Exp. Brain Res.* 60:335–349). When co-grafted with cerebral cortical or hippocampal tissue into the anterior chamber of the rat eye, adrenal chromaffin cells form nerve fibers which innervate the adjacent co-grafted brain tissue (Olson et al., 1980, *Exp. Neurol.* 70:414–426). It has also been shown that transplanted adrenal medulla tissue can correct functional deficits resulting from nigrostriatal dopamine depletion in rats (see, for example, Freed et al., 1981, *Nature* 292(5821):351–352), although dopamine secretion, and the functional improvement by the implant, decreases by about three to six months after implantation. However, NGF treatment of the transplanted cells induces fiber outgrowth from the transplant into the host and induces a longer lasting behavioral recovery (at least a year) and few implant cells survive without NGF treatment. Accordingly, in embodiments utilizing adrenal medulla chromaffin cells as the therapeutic cells, the therapeutic cells are preferably treated with a neurotrophic factor, preferably NGF, prior to implantation, and may be optionally implanted in the presence of a neurotrophic factor such as NGF.

Another source of therapeutic cells is established neural cell lines. Many neuronal clones exist which have been used extensively as model systems of development since they are electrically active with appropriate surface receptors, specific neurotransmitters, synapse forming properties and the ability to differentiate morphologically and biochemically into normal neurons. Such cells are described, for example, in the following references: Kimhi et al., 1976, *Proc. Natl. Acad. Sci. USA* 73:462–466; In: *Excitable Cells in Tissue Culture*, Nelson, P. G. et al., eds., Plenum Press, New York. 1977, pp. 173–245; Prasad et al., In: *Control of Proliferation of Animal Cells*, Clarkson, B. et al., eds., Cold Spring Harbor Laboratory Press, Cold Spring Harbor, N.Y. 1974, pp. 581–594; Puro et al., 1976, *Proc. Natl. Acad. Sci. USA* 73:3544–3548; Notter et al., 1986, *Devel. Brain Res.* 26:59–68; Schubert et al., 1970, *Proc. Natl. Acad. Sci. USA* 67:247–254; Kaplan et al., In: *Basic and Clinical Aspects of Molecular Neurobiology*, Guffrida-Stella, A. M. et al., eds., Milano Fondozione International Manarini, 1982.

Neural cell lines have a number of advantageous qualities which may be useful in the instant invention. Generally, these cells can be propagated in vitro indefinitely, which simplifies genetic manipulation of the cells. Additionally, the phenotype of differentiated cells from most neural cell lines can be manipulated by altering the culture environment. It should be noted that, due to the potential for such cell lines to form benign or malignant tumors, therapeutic cells derived from neural cell lines are rendered amitotic prior to administration in accordance with the instant invention. Therefore, in one embodiment of the present invention, cell line cells are modulated in vitro with the appropriate growth or differentiation factor and with an amitotic agent before transplantation in order to promote cell survival and prevent expression of the tumorigenic potential.

For example, human neuroblastoma cells from the IMR 32 cell line can survive and express cholinergic markers in primate brain nine months after transplantation (Gash et al., 1986, *Science* 233:1420–22). As noted above, these cells are preferably treated to render them morphologically and biochemically differentiated in vitro and must be rendered permanently amitotic before administration, which further aids in their survival (Gash et al., supra; Gupta et al., 1985, *Dev. Brain Res.* 19:21–29). Cells from the pheochromocytoma/neuroblastoma cell line, PC 12, can be stimulated to differentiate in vitro by the addition of NGF and anti-mitotic agents to the culture medium. The resulting differentiated cells produce catecholamine neurotransmitters. Neural cell lines useful as therapeutic cells in accordance with the instant invention are those neural cells lines which produce dopamine naturally, through growth factor/hormone manipulation of the cells, or through genetic engineering of the cells.

Somatic cell hybrids may also be used as a source of therapeutic cells. Somatic cell hybrids can be formed which retain the properties of differentiated cells. For example, hybrids derived from fusion of sympathetic ganglia and neuroblastoma cells can synthesize dopamine (Greene et al., 1975, *Proc. Natl. Acad. Sci. USA* 82:4923–4927). Embryonic precursors to dopaminergic neurons from the CNS can be fused with mitotic cells to incorporate both genomes into a single one that loses extra chromosomes over time and results in a new hybrid line. Methods for creating somatic cell hybrids are well known in the art and it is within the skill of the art to produce such hybrid neural or paraneural cells without undue experimentation, screen them for the desired traits (including dopamine secretion), and select those having the best potential for transplantation.

Cells which have been genetically engineered to produce a substance of neurological interest may also be used as therapeutic cells. A preferred cell type for genetic engineering is a human foreskin fibroblast, which is easily obtained and cultured. For use in the present invention, the cells are genetically altered, using methods known in the art, to express the enzymes necessary for the production of dopamine or dopamine precursors (e.g., tyrosine hydroxylase; Wolff et al., 1989, *Proc. Natl. Acad. Sci. USA* 86(22): 9011–9014, and/or L-DOPA decarboxylase, Scherer et al., 1992, *Genomics* 13(2), 469–471). See, for example. Gage et al., 1987, *Neuroscience* 23:795–807; Rosenberg et al., 1988, *Science* 242:1575–1578; Shimohama et al., 1989, *Mol. Brain Res.* 5:271–278.

The recombinant DNA molecules useful for the methods of the present invention can be produced through any of a variety of means, such as, for example, DNA or RNA synthesis, or more preferably, by application of recombinant DNA techniques. Techniques for synthesizing such molecules are disclosed by, for example, Wu et al. (1978, *Prog. Nucl. Acid. Res. Molec. Biol.* 21:101–141). Procedures for constructing recombinant molecules are well known in the art and are disclosed in detail by, for example, Sambrook et al. (supra).

Dopamine is synthesized from the amino acid tyrosine in a two step process. Tyrosine is first hydroxylated by tyrosine hydroxylase to produce L-DOPA. L-DOPA, which is utilized as a therapy in neurological disorders involving the loss of dopaminergic neurons, such as Parkinson's Disease, is converted to dopamine by L-DOPA decarboxylase. Tyrosine hydroxylase and L-DOPA decarboxylase genes are known from a number of different species, including humans.

Preferably, the cells are genetically engineered to produce "species matched" enzymes; that is, if the subject is a human, the genetically engineered dopamine pathway enzymes are also human. However, since the brain is an immunologically privileged site, it is not necessary that the genetically engineered dopamine pathway enzymes are species matched.

The gene(s) for genetic engineering may be conveniently amplified from DNA or RNA which contains the gene(s) of interest using the polymerase chain reaction or any other template-dependent amplification method, as is well known in the art. The amplified DNA is then isolated using standard techniques (such as agarose gel electrophoresis). Alternately, the gene(s) may be isolated from a DNA, typically a cDNA, library which is known or believed to contain the gene(s) of interest. The gene(s) is isolated using techniques known in the art (including nucleic hybridization screening, phage display, expression screening using soluble receptors or antibodies which bind to the desired gene product, and DNA sequencing).

Once isolated, the gene(s) is subcloned into an "expression vector" (a DNA construct which comprises the appropriate transcriptional and translational regulatory sequences to allow transcription of the gene and translation of the resulting mRNA in the therapeutic cell) such that the gene(s) is operably linked to the transcriptional and translational regulatory sequences. If more than one gene is genetically engineered into the cells, the genes are preferably linked to separate transcriptional/translational regulatory sequences.

Expression constructs for use in eukaryotic cells are well known in the art. Generally, the expression construct will comprise an enhancer, a promoter including transcriptional and translational initiation/regulatory sequences, one or more introns (which may be located at the 5' end of the gene, within the gene sequence, or at the 3' end of the gene), the gene of interest, a termination codon, 3' untranslated sequence (3' UTR), and a poly-A addition site. The precise details of the expression construct will vary according to the species and cell type of the therapeutic or support cell that is the subject of the genetic engineering, as is known in the art.

As will be apparent to one of skill in the art, the promoter, enhancer, introns, 3' UTR, and poly-A addition site may be native to the gene or may be heterologous, depending on the gene and the therapeutic cell. In most cases, the promoter will be a heterologous promoter, such as the mouse metallothionein I promoter (Hamer et al., 1982, *J. Mol. Appl. Gen.* 1:273–288); the TK promoter of Herpes virus (McKnight, 1982, *Cell* 31:355–365); the SV40 early promoter (Benoist et al., 1981, *Nature* (London) 290:304–310) and the collagen promoter (Prockop et al., 1979, *New Eng. J. Med.* 301: 13–23, 77–85; Eyre, 1980, *Science* 207:1315–1322; Martin et al., 1985, *Trends Bioch. Sci.* 10:285–287). Useful heterologous enhancers include the SV40 enhancer.

It will be apparent to one of ordinary skill in the art that cell surface markers may be utilized to select the therapeutic cells prior to administration. Specific markers can be used to select fully differentiated cells from a population of cells, or to select genetically modified cells. A number of CNS-specific markers are known which may be useful for selection of cells, including CNS-specific gangliosides, cell surface receptors for neurotransmitters and neuropeptides, and other markers as are known in the art, as are methods for utilizing these markers to select desired cells.

If the therapeutic cells are heterologous to the subject (i.e., derived from another individual and/or species), then the possibility of an immune reaction against the therapeutic cells must be considered. As discussed above, the therapeutic cells are preferably species matched. If the therapeutic cells are species matched, the risk of hyperacute rejection is of very low order. However, acute and chronic graft rejection reactions are possible. Accordingly, in certain embodiments of the invention, particularly where the therapeutic cells are not autologous, the therapeutic cells have the properties of protective cells (e.g., RPE cells) or are administered with protective cells (e.g., Sertoli cells). If the therapeutic cells are administered with separate protective cells, the two cell types may be mixed prior to or during attachment to the support matrix, or they may be separately attached to support matrices and combined immediately before or during administration to the subject. If the therapeutic cells and the protective cells are separately adhered to support matrices, the support matrices for the therapeutic cells and the protective cells may be the same or different. Generally, approximately $10^2$–$10^7$ protective cells are administered with the therapeutic cells per site of administration, preferably $10^3$–$10^6$ protective cells, although the exact number will vary depending on the properties of the protective cells (e.g., the level of expression of the immunosuppressive molecule), as will be apparent to one of skill in the art.

Cells transplanted into the mammalian brain according to the present invention can survive in the absence of added growth factors. However, in certain embodiments of the invention, the therapeutic cells are treated with a neurotrophic factor (e.g. NGF) before, during or after attachment to the support matrix, and/or may be treated with a neurotrophic factor during or after administration to the subject.

Therapeutic cells of the invention may also be implanted or injected with support cells. Glial cells normally act to support neurons in the nervous system, and grafted glial cells may play an important role in functional recovery of neurons by, for example, supplying important neurotrophic factors (Doering et al., 1984, *J. Neurolog. Sci.* 63:183–196; Gumple et al., 1984, *Neurosci. Lett.* 37:307–311). Additionally any cell of choice may be genetically engineered to supply neurotrophic factors. Accordingly, in certain embodiments of the invention, the therapeutic cells are administered to the subject in combination with support cells. The therapeutic cells may be combined with the support cells prior to or during attachment to the support matrix, or they may be separately attached to support matrices and combined immediately before or during administration to the subject. If the therapeutic cells and the support cells are separately adhered to support matrices, the support matrices for the therapeutic cells and the support cells may be the same or different. Additionally, support cells may be combined with therapeutic cells and protective cells.

Support Matrices

The support matrix is made of material which is preferably non-toxic, for example, glass, polystyrene, polypropylene, polyethylene, polycarbonate, polypentane, acrylonitrile polymer, nylon, magnetite, natural polysaccharide, a modified polysaccharide, collagen, gelatin and modified gelatin such as crosslinked gelatin.

A preferred support matrix is a microcarrier of gelatin, as described for example in U.S. Pat. No. 4,935,365. Suitable gelatin microcarriers are commercially available as Cultispher® porous microcarriers. These gelatin microcarriers have diameters ranging from 80 μm to 330 μm. Particularly preferred in the practice of the claimed invention are Cultispher-S®, porous microcarriers of crosslinked gelatin having a diameter between 80 μm to 170 μm (mean of 120 em). When using human RPE cells, it has been determined that these gelatin microcarriers adhere, on average, 24 cells per microcarrier, as compared to glass or collagen carriers (e.g., Cytodex) which adhere approximately 5–7 cells per microcarrier.

It should be noted that the support matrix of the present invention is not an encapsulating matrix or material. According to the present invention, the cells are attached to or coating the surface of the support; they are not encapsulated within a closed compartment. When attached to the support according to the present invention, the cells used for transplantation are generally on the "outer surface" of the support. The support may be solid or porous. However, even in a porous support, the cells are in direct contact with the external milieu without an intervening membrane or other barrier. Thus, according to the present invention, the cells are considered to be on the "outer surface" of the support even though the surface to which they adhere may be in the form of internal folds or convolutions of the porous support material which are not at the exterior of the particle or bead itself. It should be further noted that the support matrix of the present invention presents no requirement that the material have particular permeability properties, such as the particular molecular weigh "cut off".

The configuration of the support is preferably spherical, as in a bead, but may be cylindrical, elliptical a flat sheet or strip, a needle or pin shape, and the like. Bead sizes may range from about 10 μm to 200 μm in diameter, preferably from about 90 to about 150 μm, even more preferably around 100 μm. For a description of various microcarrier beads, see, for example. *Fisher Biotech Source* 87–88. Fisher Scientific, Co., 1987, pp. 72–75; *Sigma Cell Culture Catalog*, Sigma Chemical Co., St. Louis, 1991, pp. 162–163; *Ventrex Product Catalog*, Ventrex Laboratories, 1989; U.S. Pat. No. 4,935,365; these references are hereby incorporated by reference.

To improve cell adhesion, survival and function, the solid matrix may optionally be coated on its external surface with factors known in the art to promote cell adhesion, growth or survival. Such factors include cell adhesion molecules, extracellular matrix, such as, for example, fibronectin, laminin, collagen, elastin, glycosaminoglycans, or proteoglycans (see: Albers, B. supra, pp. 802–834) or growth factors, such as, for example, NGF. Alternatively, if the solid matrix to which the implanted cells are attached is constructed of porous material, the growth- or survival-promoting factor or factors may be incorporated into the matrix material, from which they would be slowly released after implantation in vivo.

Adhering Cells to a Support Matrix

The cells useful in the practice of the present invention can be adhered to the support matrix by any methods known in the art. Typically, cells can be adhered simply by incubating them with the support matrix. Relative amounts and concentrations of cells and microcarriers can be readily determined by those of skill in the art, but in one preferred embodiment, cells and microcarriers are mixed at a ratio of from about 5 to about 50 cells per microcarrier.

In a preferred embodiment, Cultispher® microcarriers (crosslinked gelatin) are incubated with therapeutic cells, protective cells, support cells, or any combination thereof, under conditions which promote binding of the cells to the microcarriers, for example for at least approximately 4 hours while mixing or at least approximately 15 hours without mixing, forming a cell-support complex (therapeutic cells, protective cells, support cells, or any combination thereof adhered to a support matrix). It should be noted that microcarriers should be sterilized before incubation with the cells, using a sterilization technique appropriate to the microcarrier, as will be apparent to one of skill in the art.

The cell-support complex is preferably formulated as a liquid suspension. The liquid may simply comprise a physiologically and pharmaceutically acceptable isotonic buffer or may contain additional components, including, but not limited to, nutrients, vitamins, anti-oxidants, growth factors and neurotrophic factors. In one preferred embodiment, the cell-support complex is formulated in Hank's buffered saline solution (HBSS).

Administration of Cell/Support Complex to Subjects

Methods of delivering cells to a particular site in the brain will be known to those of skill in the art. Preferably, the cell-support complex is administered directly into a particular site in the brain, for example, by injection or by implantation. To treat the negative symptoms of schizophrenia, for example, the cell-support complex may be administered into the prefrontal cortex. For improvement of cognitive deficits associated with schizophrenia, the cell-support complex is also administered to the prefrontal cortex, particularly the dorsolateral prefrontal cortex. EPS (e.g., tardive dyskinesia, tardive dystonia and/or tardive akathisia) is treated by administration of a therapeutic cell/support matrix complex to the striatal area of the subject's brain.

Typically, the site(s) of interest is identified and, using standard stereotaxic Atlas coordinates, or alternately using coordinates developed from a magnetic resonance imaging (MRI) scan, and the cell-support complex is injected. As will be apparent to one of skill in the art, needles used for injection should be selected to minimize clogging of the needle and minimize damage to the tissue at the site of injection. Accordingly, the needle size will depend on the size and shape of the support matrix.

The needle used for injection may be straight, beveled or have a bent tip. If a beveled or bent tip needle is utilized, care should be taken to correct the stereotaxic coordinates to compensate for the tip of the needle.

Alternately, the cell-support complex may be implanted. If implantation is used, the cell-support complex is preferably formulated as a slurry or a pellet. The site for implantation is identified, and the cell-support slurry or pellet is deposited at the implantation site using standard surgical techniques.

The number of cells which are administered to a particular subject will depend on a number of individual variables, as will be apparent to one of skill in the art. The severity of the disorder, the psychiatric and medical history of the subject, and the properties of the therapeutic cells are all considered when selecting the number and type of cells to administer to the subject. Generally, about $10^3$–$10^7$ therapeutic cells are administered per site, preferably $10^5$–$10^6$ cells per site, in a total of from 1 to 25 sites, more preferably 5 to 20 sites for treatment of the negative symptoms of schizophrenia, cognitive deficits associated with schizophrenia or tardive dyskinesia.

Preferably, the cell-support complex is administered to a subject suffering from the negative symptoms of schizophrenia, cognitive deficits associated with schizophrenia, or EPS on a single occasion (although the subject may receive the cell-support complex at multiple sites on that single occasion), to minimize trauma to the subject. However, as will be apparent to one of skill in the art, the cell-support matrix may be delivered to the subject in multiple doses. Preferably, any cell-support complex administered subsequent to the first occasion is administered at least one week, and preferably four weeks, after the previous occasion of administration, to allow for assessment of the subject after each administration.

Treatment of a subject suffering from the negative symptoms of schizophrenia by administration of therapeutic cells to the subject results in an improvement in the negative symptoms by, for example, alleviation or elimination of one or more of the negative symptoms, diminishment of the extent of the negative symptoms, stabilization of the subject's negative symptoms or a delay or slowing of progression in the negative symptoms. The subject's negative symptoms of schizophrenia can be measured (before, during or after the administration of therapeutic cells) using any relevant measurement device, scale or method known in the art, such as the PANSS, the SAPS, the SANS or the SCZI, preferably the PANSS.

Treatment of a subject suffering from cognitive deficit(s) associated with schizophrenia by administration of therapeutic cells to the subject results in an alleviation of the cognitive deficit(s) by, for example, improvement of cognitive function, or a delay or slowing of increased cognitive deficit(s). Cognitive function can be measured before and after treatment in accordance with the invention, using any relevant test or scale known in the art, including standard neuropsychological tests such as the Wisconsin Card Sorting Test (WCST), the Mini-Mental State Examination (MMSE), the Alzheimer's Disease Assessment Scale (ADAS) and the Clinical Global Impression (CGI), but more preferably pen and paper versions of tasks that activate Walker area 56 in non-human primates such as the working memory test described by Keefe et al. (1995, Schizophr. Res. 17(1): 25–33).

Treatment of a subject suffering from an EPS such as tardive dyskinesia, tardive dystonia and/or tardive akathisia by administration of therapeutic cells to the subject results in an improvement in the symptoms of the EPS by, for example, reduction or elimination of undirected movements, reduction, elimination or stabilization of dystonia at any particular affected site, reduction, elimination or stabilization of akathisia-related symptoms, stabilization of the subject's dyskinesia symptoms or a delay or slowing of progression in the dyskinesia symptoms. The subject's EPS can be measured (before, during or after the administration of therapeutic cells) using any relevant measurement device, scale or method known in the art, such as the Abnormal Involuntary Movement Scale (AIMS), the Barnes Akathisia Scale (BAS), the Modified Simpson Dyskinesia Scale (MSDS), and the Simpson-Angus Extrapyramidal Effects Scale (S-AS), preferably the AIMS.

The publications, patents, patent applications, and published patent specifications referenced in this application are hereby incorporated by reference in their entirety into the present disclosure to more fully describe the state of the art to which this invention pertains.

EXAMPLES

Example 1

Treatment of the Negative Symptoms of Schizophrenia by Administration of RPE cells Adhered to a Support Matrix Humans who have ingested PCP on a long term basis exhibit a large number of symptoms associated with schizophrenia, such as withdrawal, affective blunting, paranoia, delusions and hallucinations. This observation is the basis of an art accepted model of schizophrenia, which utilizes long term administration of phencyclidine (PCP) to vervet monkeys (Jentsch et al., supra)

Vervet monkeys (Cercopithecus aethiops sabaeus) are divided into three groups. The first group ("Control") are given intramuscular (IM) saline injections bid, for 14 days. The second and third groups ("PCP-" and "PCP+") are given 0.3 mg/kg PCP by IM injection, bid, for 14 days.

Human RPE cells are prepared according to the method of Lui et al. (1990, Investigative Ophthamol., ARVO Supplement). The cells are adhered to crosslinked gelatin microspheres (Cultispher-S®, mean diameter 120 µm) by mixing microspheres with cells suspended in culture medium (Dulbecco's modified essential medium (DMEM) with 10% fetal calf serum (FCS)) then incubating the mixture overnight at 37° C. in a 5% $CO_2$ atmosphere to form the cell-support complex. The cell-support complex is rinsed and resuspended in HBSS.

Cell-support complex is administered to PCP+ monkeys at 10 sites in the prefrontal cortex by stereotaxic injection. Approximately $5 \times 10^5$ cells are administered per site. Control and PCP- monkeys receive injections of an equal volume of the support matrix suspended HBSS at 10 sites in the prefrontal cortex by stereotactic injection.

After allowing the animals to recover from the surgery for one to two weeks, all monkeys are evaluated by testing prefrontal cognitive function using "object retrieval with detour task" testing. In such testing, the monkeys are trained to recover a reward from a transparent box with a single opening. The monkeys are scored on first try success rate (recovering the reward through the opening on the first try), barrier reaches (number of reaches toward the reward on a closed side of the box), and perserveration (number of repeat attempts to reach the reward through a closed side).

Example 2

Treatment of Tardive Dyskinesia by Administration of RPE Cells Adhered to a Support Matrix Long term administration of Cebus monkeys with certain antipsychotic drugs provides a model for human EPS associated with antipsychotic drug therapy, particularly TD (Kovacic et al., 1982, J. Clin. Psychopharm. 2(5):305–307). Cebus monkeys treated with long term administration of fluphenazine exhibit classic TD symptoms, including rhythmic finger movements, movements analogous to human pacing, and oral symptoms such as rhythmic up and down motions of the jaw and tongue movements.

Cebus apella monkeys are treated to produce a model of TD, by long term administration of depot fluphenazine enanthate. Fluphenazine is administered biweekly, progressing from a low dose (0.1 mg/kg) to 3.2 mg/kg by six months. Treatment is continued for at least one year.

Activity of the monkeys is observed, with particularly attention to locomotor activity and signs of TD, to establish baseline levels of EPS. The monkeys are split into two groups: control and treatment.

Human RPE cells are prepared according to the method of Lui et al. (1990, Investigative Ophthamol., ARVO Supplement). The cells are adhered to crosslinked gelatin microspheres (Cultispher-S®, mean diameter 120 µm) by mixing microspheres with cells suspended in culture medium (Dulbecco's modified essential medium (DMEM) with 10% fetal calf serum (FCS)) then incubating the mixture overnight at 37° C. in a 5% $CO_2$ atmosphere to form the cell-support complex. The cell-support complex is rinsed and resuspended in HBSS.

The cell-support complex is administered by stereotaxic injection to the striatum of treatment group monkeys, administering approximately $5 \times 10^5$ cells are administered per site at a total of 10 sites Control group monkeys receive injections of an equal volume of the support matrix suspended HBSS at 10 sites in the striatum by stereotactic injection.

Following a one to two week recovery period, control and treatment group monkeys are evaluated for locomotor activity and signs of TD.

The present invention has been detailed both by direct description and by example. Equivalents and modifications of the present invention will be apparent to those skilled in the art, and are encompassed within the scope of the invention.

The invention claimed is:

1. A method for providing dopamine or a dopamine precursor to a dopamine deficient prefrontal cortex of a subject exhibiting negative symptoms of schizophrenia or cognitive defects associated with schizophrenia, comprising administering an effective amount of a cell/support complex to the prefrontal cortex of the subject's brain, wherein said cell/support complex comprises cells adhered to a support matrix, wherein said cells produce dopamine or a dopamine precursor, wherein the cells are allogeneic, non-genetically modified retinal pigment epithelial cells, wherein said support matrix is made of a material selected from the group consisting of glass, polystyrene, polypropylene, polyethylene, polyvinylidene fluoride, polyurethane, polyalginate, polysulphone, polyvinyl alcohol, acrylonitrile polymers, polyacrylamide, polycarbonate, polypentene, polypentane, nylon, magnetite, natural polysaccharide, modified polysaccharide, collagen, gelatin and modified gelatin, and wherein said negative symptoms of schizophrenia or cognitive defects associated with schizophrenia are ameliorated.

2. The method of claim 1, wherein said cell/support complex is administered to the subject by injection.

3. The method of claim 1, wherein said cell/support complex is administered to the subject by implantation.

4. The method of claim 1, wherein said support matrix is gelatin or modified gelatin.

5. The method of claim 4 wherein said support matrix is crosslinked gelatin.

6. The method of claim 1 wherein the cells produce a dopamine precursor.

7. The method of claim 1 wherein the cells produce dopamine.

8. The method of claim 1 wherein the subject is a human.

9. The method of claim 1 wherein the cell/support complex is administered to the dorsolateral prefrontal cortex of the subject's brain.

* * * * *